Aug 6, 1974 G. MERRILL Plant Pat. 3,581
VARIETY OF NECTARINE-MAY QUEEN
Filed Sept. 24, 1971
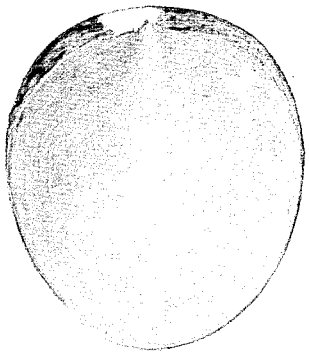
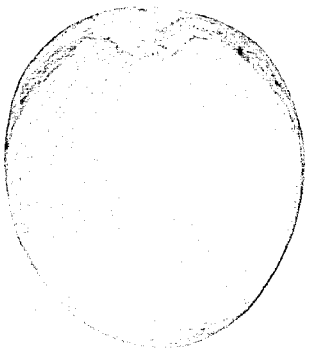
GRANT MERRILL
INVENTOR
Virgil L. Gerard
ATTORNEY

United States Patent Office

Plant Pat. 3,581
Patented Aug. 6, 1974

3,581
NECTARINE TREE

Grant Merrill, 416 N. Anderson Road,
Exeter, Calif. 93221

Filed Sept. 24, 1971, Ser. No. 183,717
Int. Cl. A01h *5/03*
U.S. Cl. Plt.—41 1 Claim

The present invention relates to a nectarine tree and more particularly to a new and improved variety thereof broadly characterized by very early ripening fruit which has a waxy, very red color over between 50% to almost 100% of its surface, is relatively large in size and has very firm flesh, by relatively very early blossoms which makes the variety especially adapted to growing in areas of relatively early production, and by its heavy and regular bearing, vigorous growing tree.

The instant variety most nearly resembles Scarlet Queen variety of nectarine (U.S. Plant Pat. No. 3,064), but differs therefrom and is an improvement thereon in that its fruit ripens five to seven days earlier and in blooming a few days earlier with lower chilling requirements, thus enabling it to be grown in areas of lower chilling requirements for normal blossoming and leafing out.

I discovered the present variety of nectarine by growing seeds of the Merrill Queen nectarine (U.S. Plant Pat. No. 2,010), open pollinated, by means of embryo-culture, on a farm in Exeter, Tulare County, Calif. The new variety of nectarine has been asexually reproduced by grafting and budding a number of test trees in various places in Tulare and Fresno Counties in California, and in each case the resulting tree and fruit characteristics were those of the original tree.

The accompanying drawing is an oil painting of a characteristic fruit showing skin color, flesh color and shape. All major color plate identifications are by reference to Maerz and Paul Dictionary of Color, First Edition.

Referring now more specifically to the pomological characteristics of this new and distinct variety of nectarine tree, the following has been observed under the ecological conditions prevailing in Tulare and Fresno Counties, California.

Tree:
- *Size.*—Large.
- *Production.*—Productive for its season.
- *Bearing.*—Regular.

Trunk:
- *Shape.*—Medium straight.
- *Color.*—Gray.
- *Texture.*—Shaggy.

Branches:
- *Size.*—Medium stocky.
- *Texture and color.*—Gray and shaggy on older branches, brown and smoother on younger branches.

Leaves:
- *Size.*—Taken from mid-portion of vigorous outside shoots 2 to 3 feet long: Medium to large—4 to 7 inches long, 1⅛ to 1⅞ inches wide.
- *Form.*—Lanceolate; tip acuminate.
- *Color.*—Medium green upper surface, lighter green under surface, very light yellow-green veins on under surface.
- *Margin.*—Crenate and glandular.
- *Glands.*—Reniform, number 2 to 7, alternate, yellow-green color, medium size.
- *Petiole.*—Medium length and size.
- *Class Meador and Blake American Society for Horticulture Science, vol. 37, pages 203–7).*—Smaller leaves 1, larger leaves 2 and 3.

Flower Buds:
- *Size.*—Medium.

- *Form.*—Plump, pubescent, free.

Flowers:
- *Size.*—Small to medium.
- *Color.*—Pinkish.
- *Quantity.*—Moderately abundant.
- *Pollen.*—Abundant.
- *Season.*—Early, with July Elberta (U.S. P.P. No. 15). First blossoms about Mar. 1, 1970, full bloom about Mar. 7, 1970—a normal year.

Fruit:
- *Maturity.*—In normal years, ready for picking about May 25 in earlier parts of Fresno and Tulare Counties, around June 1 in later parts of Tulare County.
- *Size.*—Generally large for its season. Axial diameter—1¾ to 2½ inches. Traversely in suture plane—1¾ to 2¼ inches. At right angle to suture plane—1¾ to 2¼ inches.
- *Form.*—Variable, but generally cordate; few ovate.
- *Suture.*—Shallow groove extending from base over entire circumference, discontinuous at either side of tip.
- *Dorsal surface.*—Rounded with shallow groove extending from base to near apex.
- *Cavity.*—Medium size, elongated in suture plane on both sides. Depth about ¼ inch, breadth about ¾ inch. Markings—distinct green, to yellow in more mature fruit, some red extending into outer areas where exposed to sun.
- *Base.*—Retuse to emarginate.
- *Apex.*—Cuspidate to mucronate.
- *Pistil point.*—Apical.
- *Stem.*—Length, ⅛ to 3/16 inch. Average diameter, ⅛ inch.

Skin:
- *Thickness.*—Medium.
- *Flavor.*—Sweet.
- *Tenacity.*—Tenacious to flesh when firm, slips when soft ripe.
- *Color.*—Apex end, lightest red 4–K–11 "Lacquer Red" to medium red 5–L–6 "Afghan Red" to darkest red 6–L–6 "Chianti." Stem end on hard ripe fruit and in cavity only on soft ripe fruit, yellow 17–K–1 with red blush as on apex end. Cavity and surrounding portion, yellow 17–K–1 to light green 17–K–8 on immature fruit, lightest 5–L–6 "Afghan Red" to darkest 6–L–6 "Chianti" on mature fruit, with flesh portion red.

Flesh:
- *Color.*—Lighest near stone. Yellow 9–F–1 to 9–K1 in central portion, darkest yellow 9–L–5 near skin.
- *Amygdalin.*—Moderate.
- *Juice.*—Moderate to abundant. Rich.
- *Texture.*—Firm, meaty.
- *Fibers.*—Fine, moderate.
- *Ripens.*—Slightly slower at stem end and around stone, slightly sooner at tip.
- *Flavor.*—Mild to pronounced. Sub-acid.
- *Aroma.*—Distinct.
- *Eating quality.*—Good.

Stone:
- *Type.*—Cling when hard ripe, completely free when soft ripe.
- *Fibers.*—Short, few.
- *Size.*—Generally small to medium. 1¼ to 1½ inches long. ⅞ inch wide. ⅝ to ¾ inch thick.
- *Form.*—Obovate, tip acuminate.
- *Base.*—Generally straight.
- *Hilum.*—Oval.
- *Apex.*—Acuminate.
- *Sides.*—Both equal and unequal.

*Surface.*—Irregularly furrowed on apex half, pitted on base half.

*Ventral edge.*—Many small grooves.

*Dorsal edge.*—Generally 1 to 2 deep grooves from base to near apex, discontinuous at apex.

*Color.*—When fresh-blond, lightest 11–H–6 to darkest 12–L–8.

Use:

*Keeping quality.*—Good when picked firm to hard.

*Shipping quality.*—Good.

Although my new variety of nectarine possesses the described characteristics under the growing conditions in Tulare County, Calif., having been first observed there, it is to be understood that variations of the usual magnitude in characteristics incident to the growing conditions, fertilization, pruning, thinning and pest control are to be expected.

Having thus described and illustrated my new variety of nectarine tree, what is claimed is:

1. A new and distinct variety of nectarine tree as illustrated and described, most nearly resembling Scarlet Queen (U.S. Plant Pat. No. 3,064) but differing therefrom by leafing and blooming earlier so it has lower chilling requirements, ripening its fruit five days to a week earlier, and with a darker red skin color, and characterized by a vigorous, productive tree regularly bearing fruit which is very early ripening and having a light to dark red color covering from 50% to nearly 100% of its surface, a firm flesh for long distance shipment, and with leaves and blossoms that are very early with low chilling requirements so it may be grown in earlier areas of warmer winters.

No references cited.

ROBERT E. BAGWILL, Primary Examiner